United States Patent [19]

Carbon

[11] Patent Number: 4,774,720
[45] Date of Patent: Sep. 27, 1988

[54] METHOD FOR ADJUSTING AN X-RAY DEVICE

[75] Inventor: Claude Carbon, Montmagny, France

[73] Assignee: Thomson-CGR, Paris, France

[21] Appl. No.: 890,645

[22] Filed: Jul. 30, 1986

[30] Foreign Application Priority Data

Aug. 2, 1985 [FR] France .................. 85 11887

[51] Int. Cl.$^4$ .............................. H05G 1/28
[52] U.S. Cl. .................. 378/116; 378/114; 378/108; 378/118
[58] Field of Search ............... 378/116, 118, 108, 114

[56] References Cited

U.S. PATENT DOCUMENTS 4,158,138 6/1979 Hellstrom .................. 378/116
4,439,867 3/1984 Yoshida .

FOREIGN PATENT DOCUMENTS 0022295 1/1981 European Pat. Off. .
0063644 11/1982 European Pat. Off. .
3324537 2/1984 Fed. Rep. of Germany .
2395670 1/1979 France .
2418948 9/1979 France .
2445088 7/1980 France .

*Primary Examiner*—Janice A. Howell
*Assistant Examiner*—David P. Porta
*Attorney, Agent, or Firm*—Oblon, Fisher, Spivak, McClelland & Maier

[57] ABSTRACT

The method of adjustment of an x-ray device involves a step of entry of data relating to images to be produced and of data relating to the x-ray tube to be employed, a step of computation of x-ray tube parameters and a step of adjustment of the parameters in accordance with these computations. The number of images to be produced is included in the entry of image data and performs a major role in the optimization of computation of adjustment parameters with a view to ensuring that the image-recording time is as short as possible, thereby avoiding the problem of motional blur.

2 Claims, 2 Drawing Sheets

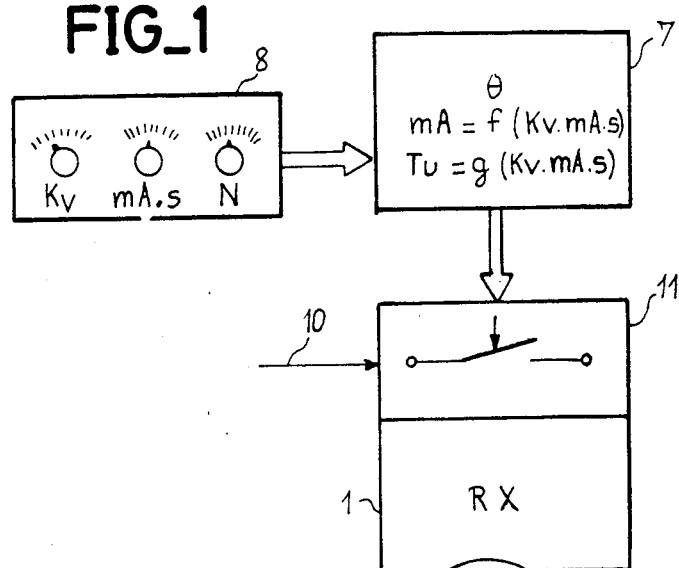
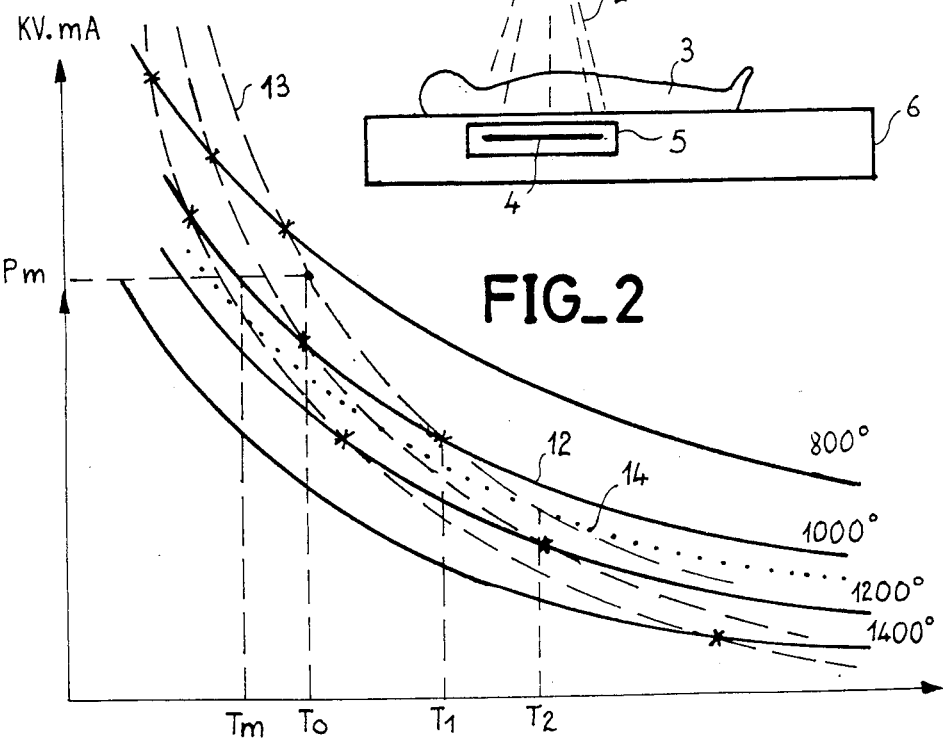

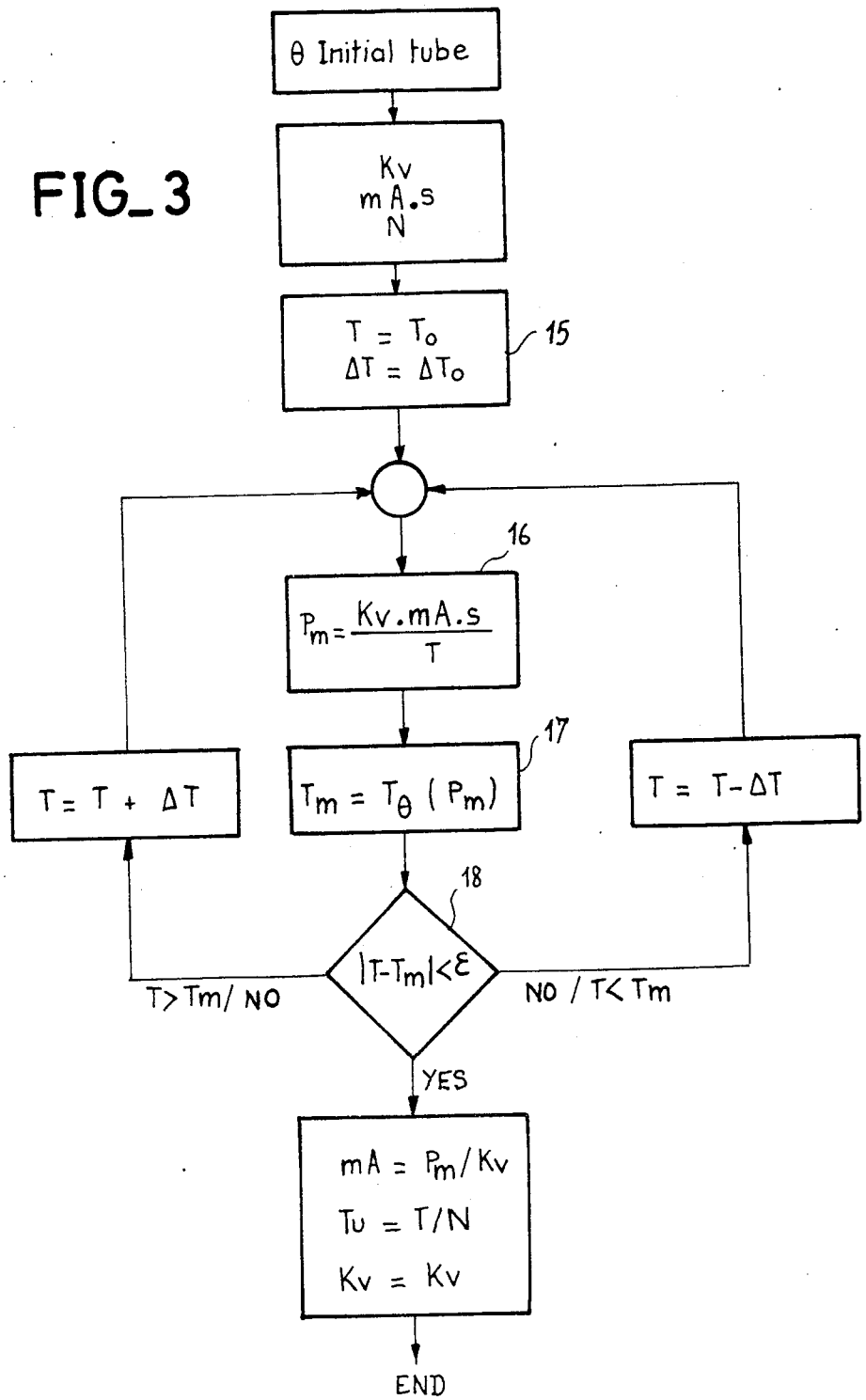

METHOD FOR ADJUSTING AN X-RAY DEVICE

BACKGROUND OF THE INVENTION

1. Field of the Invention

The present invention relates to a method for adjusting an x-ray device. More specifically, said x-ray device is of the type employed in the medical field and serves to perform radiographic and/or fluoroscopic examinations with or without the aid of luminance amplifiers.

2. Description of the Prior Art

An x-ray device is made up of an x-ray emitter, a patient support panel, and a device for measuring the irradiation produced by the x-ray tube after passage of radiation through a body positioned on the panel for examination. The measuring device can be associated with a television-type camera or a radiation-sensitive film. Handling of x-ray tubes is a difficult operation which involves electronic-electromagnetic conversion. Electrons emitted by a cathode impinge upon an anode at high velocity. Under the action of electron impacts, the anode emits the requisite x-radiation. However, the conversion ratio does not have the value of 1:1. Part of the energy of the incident electrons is converted to low-frequency electromagnetic radiation or in other words to heat. This results in heating of the anode which consequently has to be used with care.

Up to the present time, different expedients have been contemplated with a view to solving this problem. In one solution, the x-ray tubes are provided with cooling devices. In another solution, the anode of x-ray tubes is a rotating anode, with the result that the surface exposed to electron radiation is continuously renewed and, on an average, heats up to a lesser degree. In spite of these solutions, when the load imposed on the x-ray tube is too high, safety cutoff devices have to be contemplated. Thus a system of characteristic curves measured for each type of x-ray tube serves to establish in respect of given values of anode temperature and power the maximum period of time during which the x-ray tube can be employed in continuous operation before its anode attains an ultimate temperature value or temperature limit. This value cannot be exceeded without resulting in irreparable damage to the x-ray tube. The safety cutoff operation consists in continuously measuring the anode temperature and cutting-off the supply of current to the x-ray tube when the ultimate temperature is attained.

A set of procedures or methods of utilization of x-ray devices has been deduced from the above-mentioned safety cutoff operation. The methods are all based on the same principle and consist in computing the permissible operating time of the x-ray tube, on the one hand on the basis of the high-voltage power supply of the x-ray tube and the dose to be received by a radiation-sensitive receiver and on the other hand on the basis of the starting temperature of the anode. Either this utilization time is shorter than actual requirements and any experimentation is precluded since it cannot be carried on to completion or else the utilization time exceeds requirements and this results in a waste of time in the majority of cases. The anode temperature is a calculated datum which is specific to the x-ray tube at the moment of utilization. The high voltage, dose rate or sensitivity of a film are data relating to images to be produced. The high voltage of the x-ray tube governs the x-radiation spectrum or in other words the penetrating power of x-rays and is determined experimentally as a function of the zones to be imaged in a human body. The radiation dose or sensitivity of the film is a direct consequence of this high voltage and of customary practices. It corresponds to the product of the heating current of the cathode of the x-ray tube and the time-duration of cathode emission. This time-duration is of course the same as the period of utilization of the x-ray tube (utilization time). In the final analysis, the aforesaid product as expressed in milliampere-seconds (mA.s) is directly proportional to the film exposure. The film must have received a sufficient radiation dose to consider that it has been sufficiently exposed. The product of high voltage in kilovolts (Kv) and milliampere-seconds (mA.s) gives the radioelectric energy dispensed by the x-ray tube or in other words the resulting quantity of heat generated at the anode, to within the nearest conversion ratio.

In one method, for example, two radiographic data, namely kilovolts and milliampere-seconds, are set up separately by an operator. The utilization time is computed with reference to an x-ray tube load graph. The weakness of this method lies in the fact that, if several successive exposures are made, the utilization times increase in length as exposures are continued. Between each exposure, the anode temperature has in fact progressively risen and the margin of variation between the operating temperature and the ultimate temperature is diminishing. In one expedient adopted in sophisticated generators with a view to guarding against this drawback, an operator enters a coefficient k which is smaller than 1 and enables a microprocessor to compute the exposure time with a characteristic load curve which is homothetic with the real load curve within a factor k. In other words, the time-durations are not optimized and are longer by 1/k. However, when it is required to examine a human body in which there is some movement of certain parts of the body, it is necessary to choose the shortest possible time intervals in order to avoid motional blur. The conclusion is that, despite its operational reliability, this method is not the most satisfactory.

The aim of the present invention is to overcome the disadvantages mentioned in the foregoing while also simplifying the work required of the operator. In actual fact, an operator is not interested either in the anode temperature or in the factor of merit k to be attributed to an experiment. In the invention, it is only necessary to indicate the number of exposures N during which the x-ray tube is intended to operate. A microprocessor then computes the exposure times with a view to limiting them to the lowest possible values.

SUMMARY OF THE INVENTION

The present invention accordingly provides a method for adjusting an x-ray device by carrying out the following operating steps:

data relating to images to be produced by the device and relating to an x-ray tube to be employed in the device are entered into a microprocessor;

values of adjustment of the x-ray tube are computed from said data;

the x-ray tube is adjusted in accordance with these values.

The invention is essentially distinguished by the fact that:

in the data entry step, the operator indicates with respect to the images to be produced, the desired number of these images, the operating high-voltage of the x-ray tube and the dose which is necessary for a radiation-sensitive receiver to be employed in order to develop the images;

in the computation step, the adjustment values are optimized as a function of the image data and of the x-ray tube data.

BRIEF DESCRIPTION OF THE DRAWINGS

Other features of the invention will be more apparent upon consideration of the following description and accompanyings wherein:

FIG. 1 illustrates a device for carrying out the method in accordance with the invention;

FIG. 2 shows a family of parametric curves representing plot of x-ray tube load values;

FIG. 3 is an exemplified flow diagram of optimization operations to be performed by a microprocessor.

DETAILED DESCRIPTION OF THE INVENTION

FIG. 1 illustrates a device for carrying out the method in accordance with the invention. This device includes an x-ray tube 1 which is used for irradiating a body 3 with an x-ray beam 2. The radiation which passes through the body 3 produces an image on a radiation-(sensitive film 4, for example, said film being in position within a cassette-holder 5 which has been placed within a patient support panel 6, said panel being located directly beneath the patient's body 3. A microprocessor 7 receives image data, namely kilovolts determined experimentally by the nature of the body 3, milliampere-seconds determined by the radiation dose which is necessary in order to expose the film 4 and a number N which determines the number of images to be obtained. When the radiation-sensitive receiver is a film, the cassette-holder 5 is equipped with a film-changing device for positioning another film 4 beneath the radiation beam 2 each time a image has been produced. In cineradiography, or in digital applications, the necessary radiation dose is determined by the characteristics of the detectors employed. The image data, often referred to as radiological constants, are entered by means of a control console 8. The microprocessor 7 also computes the data relating to the x-ray tube, that is to say essentially the anode temperature $\theta$. This calculation is estimated in accordance with known practice and takes into account the history of operation of the x-ray tube from the time it was first put into service. With these data, the microprocessor 7 computes the exposure time and the heating current in respect of each of the N images. The microprocessor is provided with conventional means (not shown) for carrying out adjustments of the x-ray tube. A control 10 enables an operator to put the x-ray device into service once the adjustments have been completed. The time-duration or period of utilization of the x-ray tube is permitted by a switch 11 which indicates the operation of the tube during this period.

The distinctive feature of the invention lies in the fact that, in the parameters entered by means of the control console 8, the number of images to be produced is indicated thus: N. In addition, the microprocessor 7 effects optimization of time-duration of the images in order to make this length of time as short as possible.

The operation of the method in accordance with the invention will now be explained with reference to the family of curves shown in FIG. 2 and with reference to the flow diagram of FIG. 3. In FIG. 2, the parametric curves in which the parameters are set in degrees (800° to 1400°) indicate the maximum exposure time for a given power of the x-ray tube and for a given initial temperature of the anode, the ultimate anode temperature (temperature limit) being reached at the end of said maximum exposure time. In respect of a given power of the x-ray tube plotted as ordinates (Kv.mA) and in respect of a given anode temperature, it is possible to determine a maximum permissible exposure time on the axis of abscissae. At a given value of power, the possible x-ray tube utilization time will be shorter as the anode temperature is higher at the outset of the experiment. The exposure or radiation dose in milliampere-seconds (mA.s) are imposed in respect of any image to be produced. Since the high voltage is also imposed, the product is given (in Kv.mA.s). This results in the dashed hyperbolic curves of the family shown in FIG. 2. Each hyperbolic curve corresponds to a given exposure. In this invention, the time-duration $T_1$ obtained by the intersection of a load curve 12 (having as a parameter the starting temperature of the x-ray tube anode) with a hyperbola 13 (having as parameter an exposure to be made) is computed as the optimum time-duration. In the state of the technique described, the presence of the factor k led in practice to the need to retain a characteristic load-curve 14 which is homothetic with the real characteristic curve 12. This resulted in the choice of a time-duration $T_2$ which was much longer and therefore unfavorable from the point of view of motional blur.

In a preferred example, the method in accordance with the invention is carried into effect by means of a sequence of operations represented schematically by the flow diagram of FIG. 3. As a preliminary step, the microprocessor 7 records the initial temperature $\theta$ of the x-ray tube, the image data entered by means of the control console 8 as well as an arbitrary time-duration $T_0$ and an arbitrary time-duration increment $\Delta T_0$. In one example, $T_0$ has a value of 100 milliseconds and $\Delta T_0$ has a value of 10 milliseconds. The microprocessor also contains in a read-only memory (ROM) the tube data represented schematically by the family of characteristic load-curves of FIG. 2. In a first step (stage 15), a "computed" time-duration is compared with the arbitrary time-duration $T=T_0$. In a second step (stage 16), the microprocessor computes an operating power $P_m$ of the x-ray tube. This operating power is equal to the ratio of the product Kv.mA.s divided by the "computed" time-duration T and corresponds in the final analysis to a point of the curve 13. In a third step (stage 17), an operating time $T_m$ is computed. This operating time is obtained by plotting the operating power on the x-ray tube load curve considered, namely curve 12. In the example shown in FIG. 2, the value $T_m$ is smaller than the value $T_0$.

A fourth step (stage 18) consists in computing the difference between the computed time-duration which in this case has the value T and the operating time $T_m$. If this difference exceeds a given reference value $\epsilon$, the computed time-duration T is modified in the appropriate direction. Since T in the present instance is of higher value than $T_m$, it proves necessary to increase the computed time-duration T which has been selected. The time-duration T is replaced by $T+\Delta T$. This sequence of operations is accordingly continued by addition (or withdrawal) of increments of arbitrary time-duration $\Delta T$ until the values $T_m$ and T are sufficiently close to each other. In this case, each value can be considered as identical with the time-duration $T_1$. This time-duration $T_1$ is optimum from the point of view of motional blur. It is in fact worthy of note that this time-duration $T_1$ has the shortest value at which the anode considered as having a given initial temperature $\theta$ will reach the ultimate temperature at the end of the time-duration. The YES output of test stage 18 permits adjustment of the cathode current which is equal to the ratio of the last operating power $P_m$ to the high voltage (Kv) applied to the x-ray tube. The unitary time-duration $T_u$ of each image is equal to the last computed time-duration retained, divided by the number of images to be produced. The high-voltage power supply of the x-ray tube remains at the same value as the high voltage applied at the outset. Under these conditions, the method of adjustment in accordance with the invention permits optimized utilization of all x-ray devices.

What is claimed is:

1. A method for adjusting an x-ray device which has a specific operating high voltage range when operated with an associated radiation-sensitive receiver and a temperature range of operation, said method comprising the steps of:

inputting into a microprocessor data providing a predetermined number of images to be formed, data providing a predetermined high-voltage of operation and data indicating a predetermined dosage to be employed with said radiation-sensitive receiver, said data input also providing input relating to the condition of said x-ray tube;

computing from said input data a series of values of adjustment of said tube wherein said values of adjustment are optimized as a function of said input data relating to said images and said input data relating to the condition of said x-ray tube wherein optimization is achieved by computing the adjustment values in order to provide that the image recording times correspond to the shortest possible time intervals;

adjusting said x-ray tube in accordance with said optimized values of adjustment.

2. A method according to claim 1, wherein said time intervals are optimized by selecting an arbitrary time-duration and an increment of arbitrary time-duration, by computing an x-ray tube operating power relative to said arbitrary time-duration and to the image data entered, by computing an x-ray tube operating time relative to said operating power and to the x-ray tube data, optimization of the operating time being achieved by addition or withdrawal of increments of arbitrary time-duration in order to ensure that there is a given small difference between said operating time and the arbitrary time-duration.

* * * * *